United States Patent [19]

Tortella et al.

[11] Patent Number: 6,046,200
[45] Date of Patent: Apr. 4, 2000

[54] COMPOSITIONS HAVING NEUROPROTECTIVE AND ANALGESIC ACTIVITY

[75] Inventors: Frank C. Tortella, Columbia, Md.; Mark A. DeCoster, Metairie, La.; Kenner C. Rice, Bethesda; Sylvia N. Calderon, Potomac, both of Md.

[73] Assignees: The United States of America as represented by the Secretary of the Army; The United States of America as represented by the Department of Health and Human Services, both of Washington, D.C.

[21] Appl. No.: 09/009,307

[22] Filed: Jan. 20, 1998

Related U.S. Application Data

[63] Continuation-in-part of application No. 08/502,468, Jul. 14, 1995, abandoned, which is a continuation-in-part of application No. 08/302,431, Sep. 9, 1994, abandoned.

[51] Int. Cl.[7] ................... A61K 31/395; A61K 31/495; A61K 31/50
[52] U.S. Cl. .................. 514/250; 514/247; 514/248; 514/249; 514/255; 514/292
[58] Field of Search ................ 514/210, 255, 514/292, 247, 248, 249, 250

[56] References Cited

U.S. PATENT DOCUMENTS

| | | | |
|---|---|---|---|
| 4,816,416 | 3/1989 | Averback | 436/166 |
| 5,552,404 | 9/1996 | Chang et al. | 514/255 |
| 5,574,159 | 11/1996 | Chang et al. | 544/396 |
| 5,658,908 | 8/1997 | Chang et al. | 514/252 |
| 5,681,830 | 10/1997 | Chang et al. | 514/85 |
| 5,854,249 | 12/1998 | Chang et al. | 514/255 |

OTHER PUBLICATIONS

Calderon et al., "Probes for Narcotic Receptor Mediated Phenomena . . .", J. of Medicinal Chemistry, 37(14), Published Jul. 8, 1994, pp. 2125–2128.

Rothman et al., "Excitotoxicity and the MNDA Recptor—Still Lethal After Eight Years", Trends in Neuroscience, 18(2), pp. 57–58.

Choi, D.W., "Calcium: Still Center-Stage in Hypoxic–Ischemic Neuronal Death", Trends in Neuroscience, 18(2), pp. 58–60.

Knapp et al., "Structure–Activity Relationships for SNC80 and Related Compounds at Cloned Human Delta and Mu Opioid Receptors", J. of Pharmacology and Experimental Therapeutics.

Vol. 277, No. 3, Published in Jun. 1996, pp. 1284–1291.

*Primary Examiner*—Robert H. Harrison
*Attorney, Agent, or Firm*—Charles H. Harris

[57] ABSTRACT

Compounds of the formula:

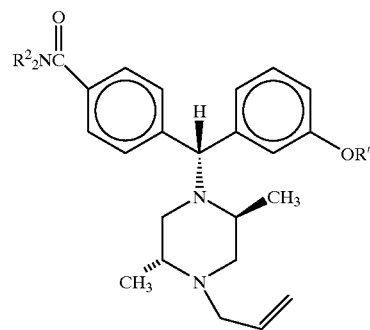

wherein $R^1$ and $R^2$ are alkyl of 1–8 carbons have been shown to have both neuroprotective and analgesic activities. The compounds of the invention may be used in treatment of conditions that would normally result in neuronal damage, including those arising on account of cerebral ischemia/hypoxia or increase in intracranial pressure such as neoplasms, stroke, meningitis or trauma. Compositions of the invention can also be useful for treatment of toxin-related damage such as drug over-dose or exposure to toxins in the environment.

6 Claims, No Drawings

COMPOSITIONS HAVING NEUROPROTECTIVE AND ANALGESIC ACTIVITY

This application is a continuation-in-part of U.S. Ser. No. 08/502,468, filed Jul. 14, 1995, now abandoned, which is a continuation-in-part of U.S. Ser. No. 08/302,431, filed Sep. 9, 1994, now abandoned.

FIELD OF THE INVENTION

This invention involves means for treating neuronal injury and achieving analgesia by administration of compositions containing compounds of the formula:

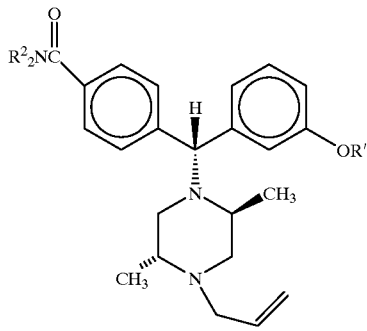

wherein $R^1$ and $R^2$ are alkyl having 1–8 carbon atoms.

BACKGROUND OF THE INVENTION

Compounds having an N-diphenylmethyl-N'-substituted piperazine have been known as antihistamines. One compound of the class, 1-p-chlorobenzyhydryl-4-[2-(2-hydroxyethoxy)ethyl]-piperazine, has been shown to be useful in treatment of anxiety and neurotic conditions when given in dosages of 400 mg. per day. The compound has also been used for treatment of alcoholism.

Recently, patent publication WO 93-GB216 disclosed a class of diarylmethylpiperazines and piperidines which were suggested to have analgesic activity. There is no teaching of a compound of the invention wherein the substituent designated OR in this application is an alkoxy.

Calderon, et al, have discovered that certain stereoisomers of diarylmethylpiperazines are particularly effective at binding in the rat brain membranes. It was suggested that certain selected compounds of a group of diarylmethylpiperazines are useful for studying the role of the opioid receptor in drug-seeking behavior.

One of the compounds of Calderon, et al., showed evidence of 1996 fold δ selectivity in μ/δ binding studies of opioid receptors.

DESCRIPTION OF THE INVENTION

It is the purpose of this invention to provide means of obtaining analgesic and neuronal protective benefits by administration of various isomers of 1-allyl-2,5-dimethyl-4-benzylhydryl compounds of the formula:

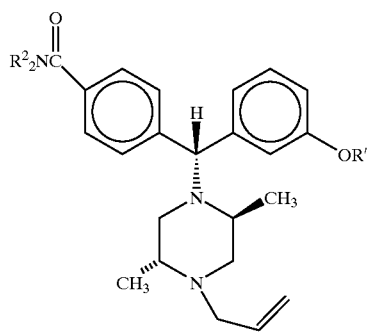

for use as analgesics and as neuronal protective agents. Compositions of the invention may be administered orally, rectally, parenterally or transdermally. Parenteral administration includes, but is not limited to, intradermal, subcutaneous, intravenous and intramuscular methods. When used as neuronal protective agents, intrathecal administration may be appropriate. While dosage will vary, the compositions of the invention will generally be given in dosages of 0.1 to 500 mg/Kg/da. In larger mammals such as man, dosage of 0.1 to 50 mg/Kg/Da are appropriate with 1–20 mg/Kg/da being a more usual range. However, when the compositions are targeted directly to neuronal tissue for protective benefit by means such as intrathecal injection, dosages of 1–1000 micrograms may be adequate. It is, of course, expected that the medical practitioner will adjust dosage to meet the particular needs of the patient depending on size and condition of the patient and on the mode of administration.

One particularly valuable enantiomer of the invention is the (+)-8 compound designated SNC80. Unlike other peptide and non-peptide opioids, high intracerebral ventricular dosages of SNC80 (up to 800 μg) failed to elicit convulsive activity in rats. To obtain better understanding of the benefits obtained by use of the compounds of the invention, beneficial effects of the compound were assessed in a model for evaluation of CNS excitotoxicity in an in vitro neuronal culture model. The neurotoxicity/neuroprotection was assessed 18 hours after exposure to the excitotoxin glutamate. LDH measurements and morphological evaluation revealed that that compound produced a concentration-dependent neuroprotection. Compared to glutamate alone, the compound protected neurons in a dose-dependent manner. When intracellular calcium was monitored as an indicator of glutamate-induced neuronal injury, treatment with SNC-80 resulted in a beneficial shift in the intracellular $Ca^{++}$ concentration, predictive of high neuroprotective activity.

Therapeutic compositions of the invention may be administered in the usual pharmaceutically acceptable carriers, depending on the method of administration. The compounds are more soluble at pH of <8, with the preferred pH range of 3.5 to 7. Compositions for intravenous administration are isotonic solutions. For intrathecal administration, carriers often would contain glucose. Examples of appropriate carriers are 5% dextrose, Ringer's lactate solution or normal saline.

Formulations for oral administration may contain inert carriers such as starches and may be in forms usually given orally such as tables or capsules. Enteric coatings such as those used to make enterically coated capsules or spansules that are then placed in capsules are appropriate.

Compositions of the invention would be useful in treatment of conditions that would normally result in neuronal damage, including those arising on account of cerebral ischemia/hypoxia or increase in intracranial pressure arising from pathologies such as neoplasms, stroke, meningitis or trauma. Compositions of the invention may also be useful for treatment of toxin-related neuronal damage for which compositions of the invention are deemed appropriate include, but are not limited to, multiple sclerosis, Alzheimer's disease, myotrophic lateral sclerosis, Huntington's chorea, Parkinson's disease and senile dementia. Other causes of neuronal damage include toxic effects resulting from disease conditions such as hepatitis, uremia and kernicterus.

A receptor chiral agonist of the formula:

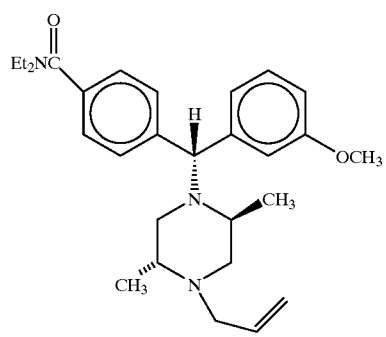

had previously been reported. However, no pharmaceutical compositions were disclosed and no method of achieving a therapeutic response was taught. It is now possible to obtain specific isomers by use of the 1-allyl-trans-2,5-dimethyl-1,4-piperazine and the benzylhydryl chloride by the method shown graphically below:

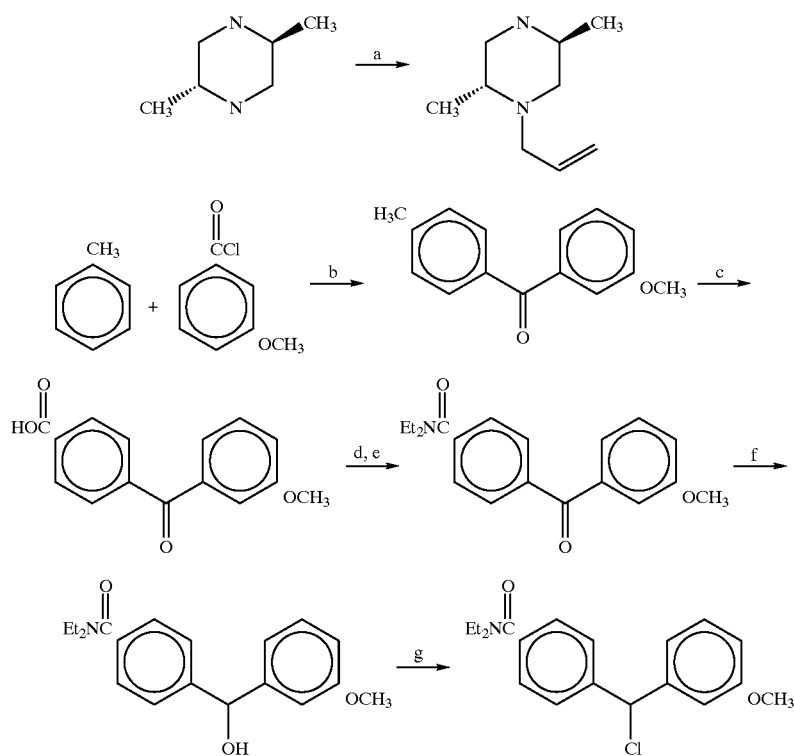

(a) Allyl bromide (50%); (b) AlCl$_3$ (84%); (c) KMnO$_4$ (53%); (d) SOCl$_2$; (e) 44% EtNH (90%); (f) NaBH$_4$ (70%); (g) 36% HCl (90%).

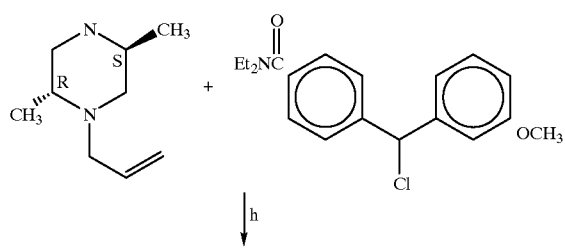

-continued

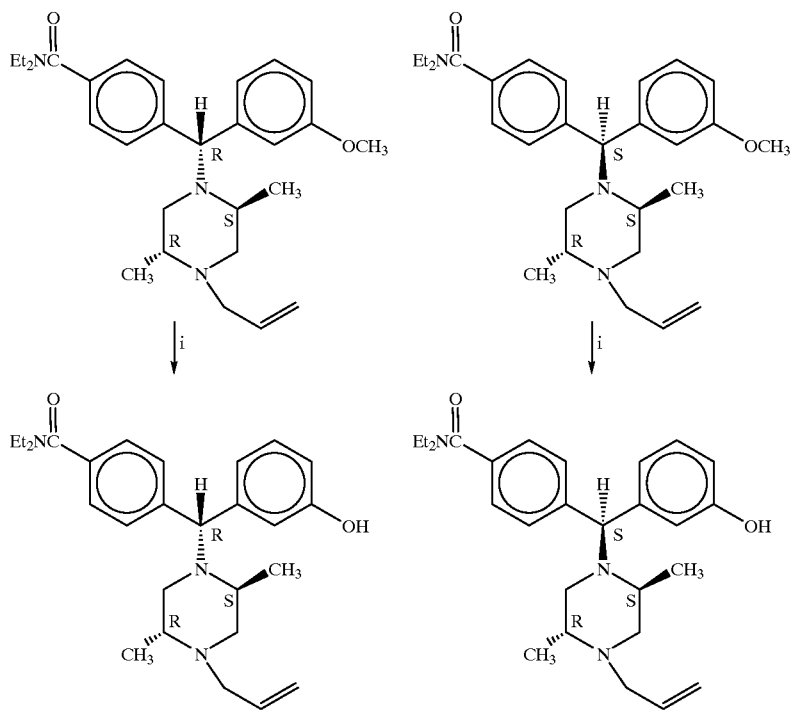

(h) K$_2$CO$_3$/acetonitrile (65%); IBBr$_2$ (45%).

This route offers the advantage that it requires only one optical resolution, that of the 1-allyl-trans-2,5-dimethyl-1,4-piperazine (±)-2, to obtain the enantiomers of formula I and its benzylic epimers. Optical resolution of the (+)-2 with (+)- and (−)- camphoric acids provided the enantiomers. Optical purity of (+)-2 and (−)-2 was determined to be >98% by NMR of the ureas formed with optically pure α-methylbenzyl isocyanate and was determined to be 99% by HPLC of the ureas formed with 1-naphthyl-isocyanate on a Ceracel OD chiral column. The optically pure (+)- enantiomer of 1, its benzylic epimer (+)-10, and their methyl ethers (+)-8 and (+)-9 were prepared as shown in Scheme 2. Repetition of Scheme 2 with Piperazine (+)-2 provided the corresponding (−)- enantiomers of these compounds.

In addition to the (+)-8(αR,2R,5S) configuration, (−)-8 (αS,2R,5S), (−)-9(αR,2R,5S), (+)-9(αS,2S,5R) and (−)-1 (αS,2R,5S) are also particularly preferred compounds.

The neuroprotective effect of the SNC80 against glutamate toxicity in neuronal cell cultures was determined using a standard method of quantifying neuronal damage by measuring LDH release, since LDH is a lysosomal enzyme released from damaged neurons into the culture media when neuronal cells are injured. One way in which neuronal cells may be damaged is by exposure to glutamate, a common agent used to induce neuronal damage. In the instant case, the damaging effect of gluamate on these cultures as shown to be overcome by exposure to an active agent of the invention.

TABLE I

| Treatment | LDH release* | % neuroprotection |
|---|---|---|
| Basal (no treatment) | 74.0 ± 3.3 | — |
| Glutamate (80 μM) | 103.9 ± 7.8 | — |

TABLE I-continued

| Treatment | LDH release* | % neuroprotection |
|---|---|---|
| Glutamate + SNC80 (5 μM) | 98.6 ± 4.5 | 17% |
| Glutamate + SNC80 (20 μM) | 91.0 ± 2.0 | 43% |
| Glutamate + SNC80 (40 μM) | 84.7 ± 3.4 | 63% |

*(Units ML ± s.e.)

The induced antagonism of glutamate neurotoxic calcium flux was studied with the results shown in Table 2.

TABLE 2

| | | Response Type | | |
|---|---|---|---|---|
| treatment | # neurons | transient | biphasic | sustained** |
| 80 μM glutamate | 18 | 4 | 0 | 14 |
| Glutamate + 50 μM SMC80 | 10 | 3 | 6 | 1 |
| Glutamate + 100 μM SNC80 | 21 | 3 | 17 | 1 |

**(neurotoxic)

Compositions of the invention are prepared by methods usual in the art. Below are examples of such compositions Capsules are prepared containing 100 mg. of SNC80 and 400 mg. of corn starch. After mixing, the mixture is packed into an empty gelatine capsule.

Tablets may be prepared using the mixture of SNC80 and starch prepared above. The mixture is pressed in a tableting press.

To provide a composition for intravenous administration, 400 mg of the (−)-9 (αR,2R,5S) enantiomer is dissolved in 5 ml of sterile half-normal saline which is buffered to a pH of 4.5. The composition is placed in a sterile vial and sealed.

To provide a composition for intrathecal injection, 400 mg of the enantiomer is dissolved in 5% dextrose in half-normal saline which has been buffered to a pH of 5.5.

Compositions containing the active agents disclosed herein may be administered in admixture with other active agents such as glutamine antagonists, calcium channel blockers, vasodilators and anticoagulants.

What is claimed is:

1. A method of protecting a mammal diagnosed as having a condition which results in neuronal damage from such neuronal damage by administration of a neuronal-protective amount of an active agent of the formula:

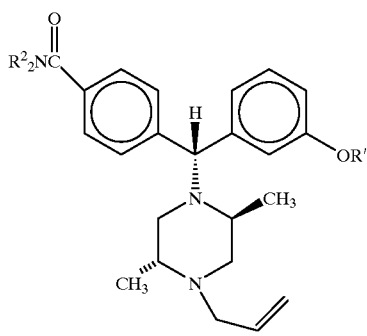

wherein $R^1$ and $R^2$ are alkyl of 1–8 carbons, in a pharmaceutically acceptable carrier.

2. A method of claim 1 wherein said active agent is the compound wherein $R^1$ is methyl, $R^2$ is ethyl in the (+)-8 (αR,2S,5R) configuration.

3. A method of claim 1 wherein said active agent is the compound wherein $R^1$ is methyl and $R^2$ is ethyl in the (−)-8(αS,2R,5S) configuration.

4. A method of claim 1 wherein said active agent is the compound wherein $R^1$ methyl and $R^2$ is ethyl in the (−)-9 (αR,2R,5S) configuration.

5. A method of claim 1 wherein said active agent is the compound wherein $R^1$ methyl and $R^2$ ethyl in the configuration (+)-9(αS,2S,5R).

6. A method of claim 1 wherein said active agent is the compound wherein $R^1$ is methyl and $R^2$ is ethyl in the configuration (−)-1(αS,2R,5S).

* * * * *